United States Patent [19]

Kato

[11] 4,222,869
[45] Sep. 16, 1980

[54] DIALYZING METHOD OF BLOOD IN ARTIFICIAL KIDNEY

[76] Inventor: Isamu Kato, 2-6 Akebono-cho, Showa-ku, Nagoya-shi, Aichi-ken, Japan

[21] Appl. No.: 946,556

[22] Filed: Sep. 28, 1978

[30] Foreign Application Priority Data

May 31, 1977 [JP] Japan .................................. 52-116456

[51] Int. Cl.² ............................................ B01D 13/00
[52] U.S. Cl. .............................. 210/646; 210/321 B;
210/356; 128/214 R; 128/214 F; 128/273
[58] Field of Search ..................... 210/22, 23 R, 23 F,
210/321 B, 416 M, 356; 128/214 R, 214 F, 273,
DIG. 3

[56] References Cited

U.S. PATENT DOCUMENTS 3,864,248  2/1975  Granger et al. .................. 210/321 B
3,894,950  7/1975  Ayres et al. ........................... 210/356

FOREIGN PATENT DOCUMENTS 2334230  1/1975  Fed. Rep. of Germany ......... 210/23 F
2276856  1/1976  France ................................. 210/321 B Primary Examiner—Ferris H. Lander
Attorney, Agent, or Firm—Armstrong, Nikaido, Marmelstein & Kubovcik

[57] ABSTRACT

Dialyzing elements of capsule form are constituted in a blood circulation path of a dialyzing membrane. Pulse pressure variation is applied to a dialyzing liquid which circulates within the dialyzing vessel in contact with the surface of the dialyzing elements. The pulse pressure variation of the dialyzing liquid causes the tension of the dialyzing membrane surface to vary the diameter of discharge hole on the dialyzing membrane is decreased and increased repeatedly, thereby toxins such as the harmful substances removed by the kidney, which are contained in the blood can be selectively separated and removed so as to carry out blood dialysis.

3 Claims, 24 Drawing Figures

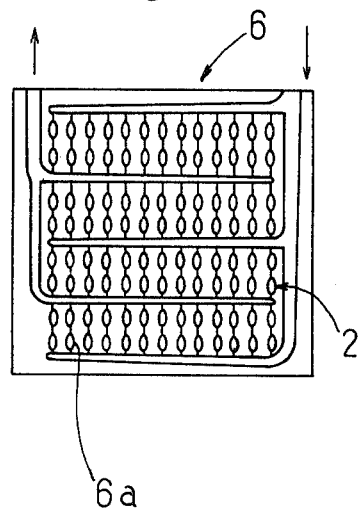
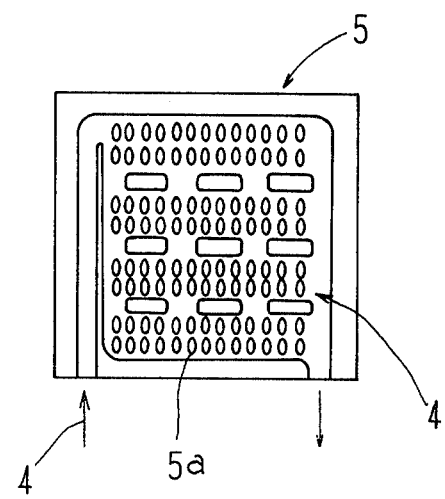
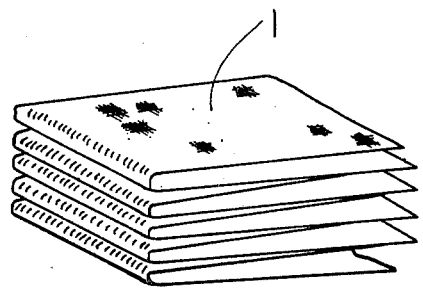
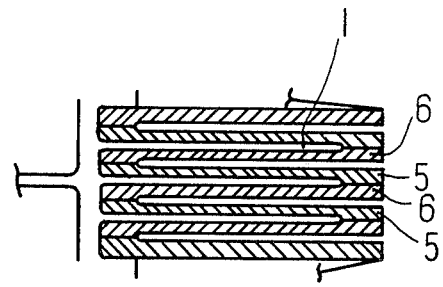

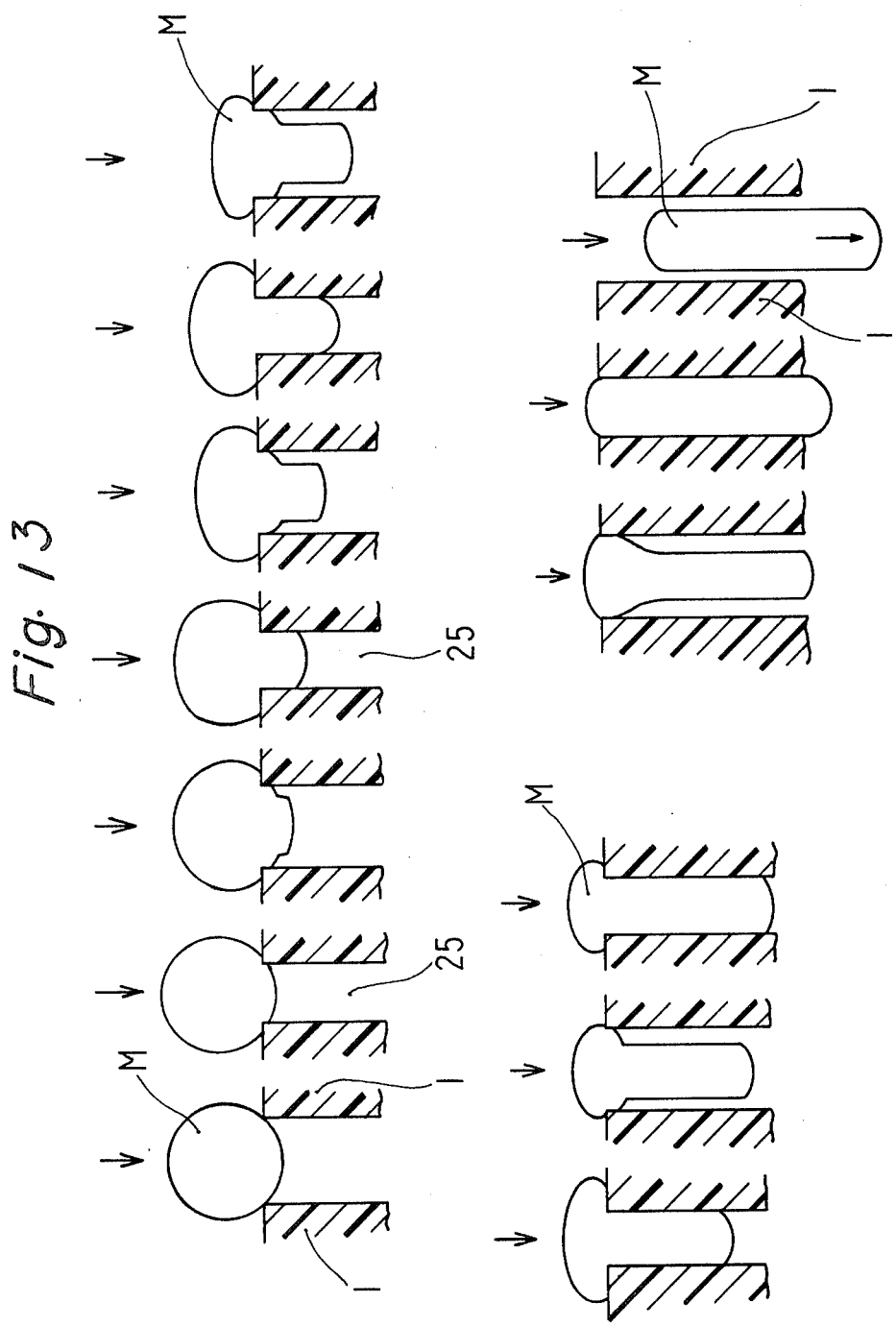

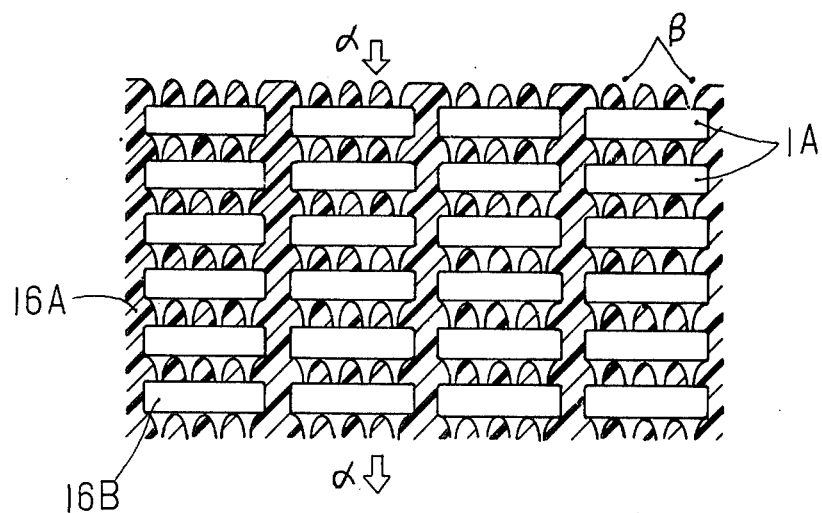
Fig. 16 A
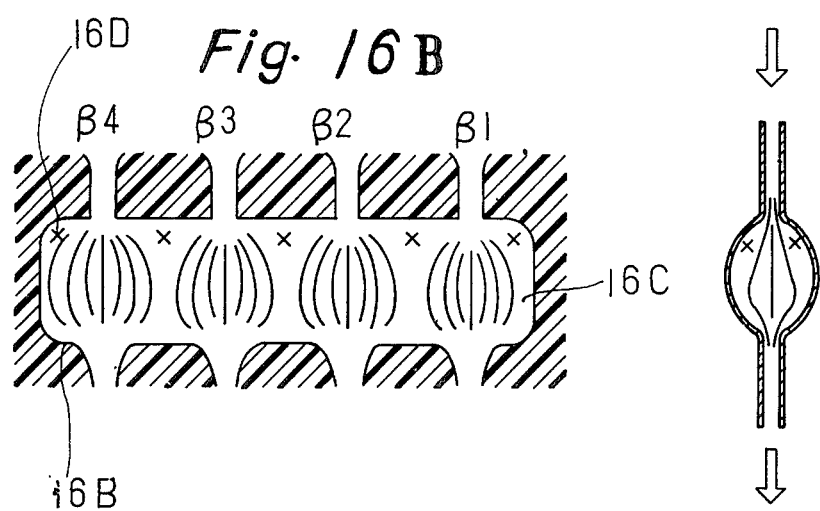
Fig. 16 B
Fig. 16 C

DIALYZING METHOD OF BLOOD IN ARTIFICIAL KIDNEY

BACKGROUND OF THE INVENTION

The present invention relates to a method of dialyzing blood using an artificial kidney, including a flat membrane system wherein blood flows between semipermeable membranes of multi-plate form and a dialyzing liquid comes into contact with blood through the dialyzing membrane so as to clarify the blood, or a hollow pipe system wherein blood is clarified during circulation in a number of hollow pipes, more particularly it relates to a blood dialyzing method which enables one to remove toxins, such as harmful substances which are removed by the kidney, such as methyl guanidine, guanidinosuccinic acid contained within blood, which cannot be easily removed by a conventional dialyzing membrane.

In general, artificial kidneys perform the functions of bringing blood into contact with a dialyzing liquid through a dialyzing membrane, removing harmful substances, such as water, urea, uric acid, creatinine, electrolytic substances including sodium ions and magnesium ions, sulfate radical, and phosphate radical contained within the blood, and adding filling-up substances from the dialyzing liquid, such as calcium ions, grapesugar, and water, to the blood.

At present, an artificial kidney functions to remove waste products; and "toxins" generally means such harmful substances as cannot be easily removed by a dialyzing membrane.

Toxins are organic substances of higher or medium molecular weight (The medium molecular weight ranges from 300 to 3000.). Toxins have such dimension that they cannot pass through small holes having a diameter of 20~30 Å on a dialyzing membrane which is thought optimum in its function at present. If the diameter of small holes on the dialyzing membrane is enlarged, other useful substances are also removed causing a bad effect on the blood. Toxins include, for example, methyl guanidine or guanidino-succinic acid having large viscosity. Blood contains useful sobstances such as various amino acids, vitamines, and hormones. These substances are as large as, but not as viscous as toxins.

In a conventional artificial kidney using a dialyzing liquid, there is a flat membrane system wherein blood is clarified during its flow between semipermeable membranes of a multi-plate form and a hollow pipe system wherein the blood is clarified during circulation in a number of hollow pipes. Such systems can dialyze substances, for example, water, creatinine, sodium ions, potassium ions, sulfate radical, and phosphate radical, which are smaller than the inner diameter of the discharge hole on the dialyzing membrane, however, they cannot remove said toxins which are larger than the discharge hole diameter.

In recent years, methods of removing these toxins are being investigated. In one method, for example, blood-plasma which contains toxins and also useful substances such as hormones is separated, in turn said contained substances are adsorbed in activated carbon. This method, however, has disadvantage in that useful substances for human bodies, such as hormones, may also be removed.

In another method, blood-plasma which contains toxins together with useful substances such as hormones and vitamins, is separated in a dialyzing liquid by means of a filtering process, in turn substitutive plasma is supplied. Such substitutive plasma is not the same as proper blood-plasma in all properties. Therefore, the method is not sufficient to moderate the condition of a patient, and it must be further improved at all points.

BRIEF SUMMARY OF THE INVENTION

An object of the present invention is to provide a dialyzing method of blood wherein toxins and other harmful substances are selectively dialyzed from blood.

Another object of the present invention is to provide a dialyzing method of blood wherein harmful substances, including toxins are effectively dialyzed from the blood.

In this invention, applying a pulse pressure variation to a dialyzing liquid produces repeated expansion and contraction of innumerable holes on a dialyzing membrane, thereby toxins having a large viscosity and elasticity and greater diameter than that of small hole of the dialyzing membrane can be squeezed out of the small holes and dialyzed, while useful substances such as vitamines, hormones and the like which are as large as but less viscous than toxins, float in the blood-plasma and cannot be squeezed out of the small holes.

A number of so-called dialyzing elements of capsule form are arranged on the blood circulation path in a dialyzing vessel to prevent the pressure variation of the dialyzing liquid from producing a flow rate variation of the blood. When the ratio of volume occupied by blood-plasma in the capsule form is increased and moreover the capsule form is made small, ratio of blood-plasma in relation to blood within the capsule is increased, thereby dialysis of harmful substances including toxins may be carried out more efficiently.

The above and further objects and features will be apparent from the following description taken in connection with the accompanying drawings. It is to be expressly understood, however, that the drawings are for purpose of illustration only and is not intended as a definition of the limits of the invention.

BRIEF DESCRIPTION OF DRAWINGS

FIG. 5 is a plan view of blood surface of the lower holding plate;

FIG. 6 is a plain view of dialyzing surface of the upper holding plate;

FIG. 7 is a perspective view of a dialyzing membrane;

FIG. 8 is a view illustrating assembling state of the dialyzing membrane with upper and lower holding plates;

FIG. 13 is a schematic view illustrating that toxins are squeezed out of discharge holes on the dialyzing membrane;

FIG. 16A is a schematic view of section of a number of dialyzing elements arranged within the dialyzing vessel;

FIG. 16B is a view illustrating blood and plasma layer within the dialyzing element; and FIG. 16C is a view illustrating longitudinal section of FIG. 16B.

DETAILED DESCRIPTION OF THE INVENTION

Embodiment of the present invention will be explained.

It is through that toxin is an elastic body with a large viscosity as above described. Therefore a dialyzing membrane of good dialyzing effect preferably has small sliding friction and small thickness, and moreover innumerable holes on the membrane are of equal diameters. At present, membranes of cellulose or acrylnitrile are used. Teflon membrane is better than those of cellulose or poly-acrylnitrile in sliding friction, but it is worse in intensity of molding. Therefore, it must be held in the molding state with the aid of holding plate. If semipermeable membranes of inferior molding property and superior dialyzing effect are developed in the future, dialyzing elements can be constituted also in this case with the aid of the holding plate.

The state of blood which flows through a blood vessel will be considered. When the diameter of the blood vessel is small, red corpuscles gather towards the center axis apart from the vessel wall on account of the so-called center concentrating effect. Therefore, the plasma layer is constituted near the vessel wall. The thickness of the plasma layer is a few microns and independent of the diameter of the blood vessel. The smaller the radius of the blood capillary becomes, the more the ratio of the plasma layer of lower viscosity in relation to the layer including blood corpuscles of higher viscosity increases.

Blood shows non-Newtonian viscosity which decreases as the diameter of the blood vessel decreases. Therefore, in the blood capillary, blood corpulscles flows more rapidly than blood-plasma. When the blood flowing through the blood capillary is suddenly introduced to the blood vessel of larger diameter, blood corpuscules of larger mass and larger flow rate tend to go right on and do not diffuse rapidly. An air gap produced in this manner is naturally apt to be filled by the plasma layer near the wall. When the plasma layer of a few microns is suddenly enlarged, the scope of the molecular movement of substances contained in the plasma layer is enlarged. Utilizing this effect, capsule forms of the dialyzing membrane having semipermeable property are constituted.

The blood circulation path of a capsule form constituted from a dialyzing membrane is called dialyzing element S.

Figure 1:
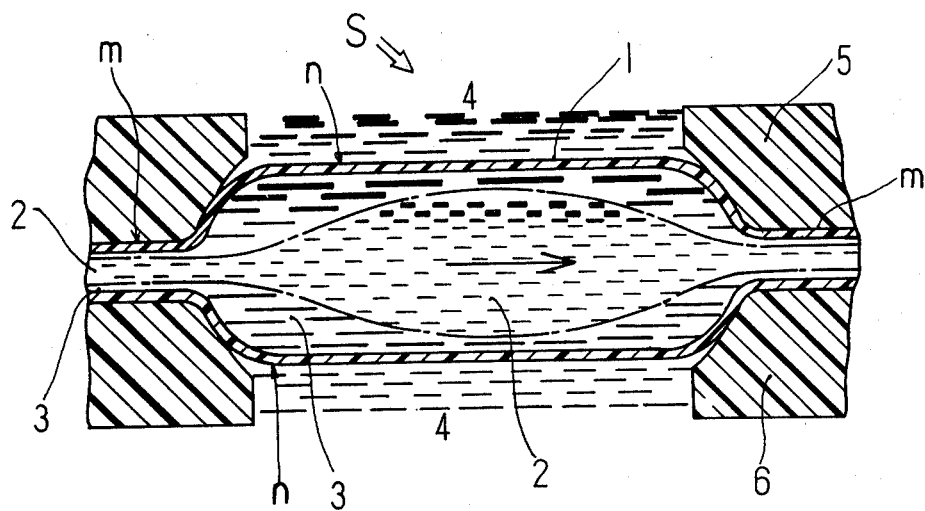
FIG. 1 is a schematic sectional view of so-called dialyzing element, i.e., blood circulation path of capsule form which is constituted by a dialyzing membrane embodying the present invention.

Referring to FIG. 1, in the circulation path of the blood which consists of a dialysis membrane 1 of semipermeable property, when blood is suddenly introduced from a circulation path m of smaller diameter to a capsule-formed circulation path n of larger diameter, in the circulation path m of smaller diameter the blood flow produces a core 2 (red corpuscles, white corpuscles, blood-platelets and blood-plasma) and a plasma layer 3 of a few microns on the wall. While in the capsule-formed circulation path n of larger diameter the core 2 is enlarged and the thick plasma layer 3 is produced on the wall.

Since the thickness of the blood plasma layer 3 in the capsule-formed circulation path n of dialytic element S is greater than that in the circulation path m with smaller diameter in normal state, molecular movement of various substances contained in the blood plasma layer 3 in the capsule-formed circulation path n may be carried out freely due to fewer occurrences of collision with the core 2. Thus, resulting in significantly better dialyzing efficiency than that of a conventional blood circulation path. Moreover, the outer circumference of the capsule-formed circulation path n is filled with a dialyzing liquid 4.

Figure 2:
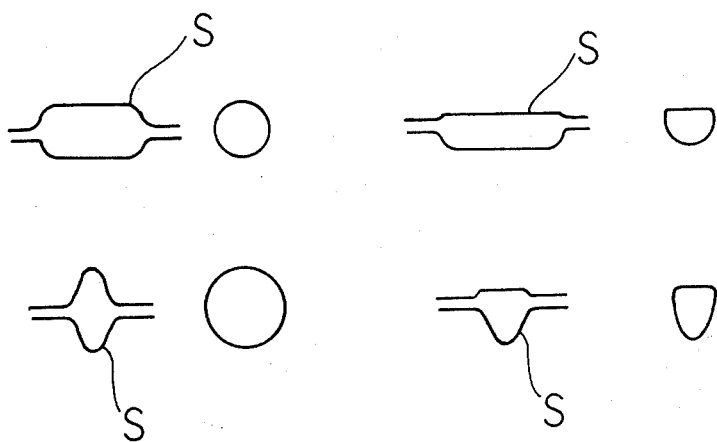
FIG. 2 is a schematic view of various capsule forms.

Known vessel may be used as the dialyzing vessel of the present invention. However, the dialyzing vessel T having so-called dialyzing element S which constitutes the blood circulation path n of capsule form conprising the dialyzing membrane 1 has a good dialyzing efficiency as above discribed. Now, the dialyzing vessel T having the dialyzing element S will be explained. Referring to FIG. 1, the dialyzing vessel T comprises a number of dialyzing elements S each of which constitutes the capsule-formed circulation path n. Referring to FIGS. 3–6, an upper holding plate 5 and a lower holding plate 6 which are made of metal such as stainless steel or plastics such as high pressure polyethylene of low density, are provided with a number of slots h arranged on respective surfaces. The blood surface is constituted symmetrically on the upper surface of the lower holding surface 6 and the lower surface of the upper holding surface 5, while the dialyzing liquid surface is constituted symmetrically on the upper surface of the upper holding plate 5 and the lower surface of the lower holding plate 6. In addition, various types of capsule forms of the dialyzing elements S can be used, examples of which are shown in FIG. 2.

Referring to FIGS. 7 and 8, where the dialyzing membranes 1 is arranged between the upper holding plate 5 and the lower holding plate 6.

Figure 9:
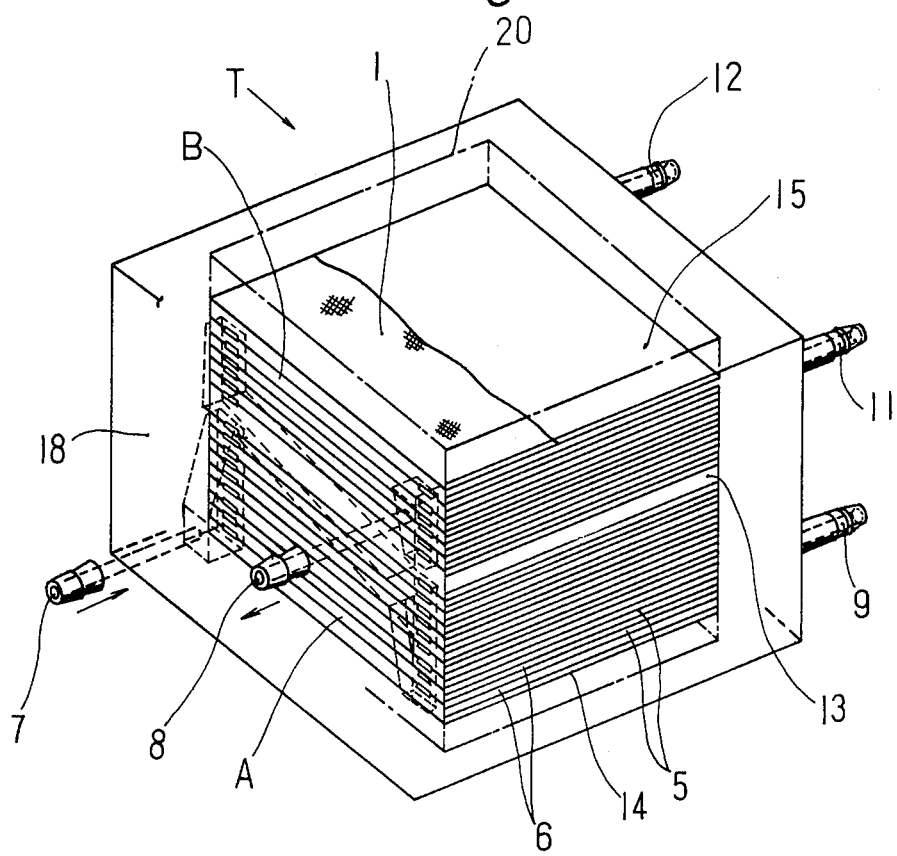
FIG. 9 is a perspective view of blood side of a dialyzing vessel comprising a negative pressure part and a positive pressure part.
Figure 10:
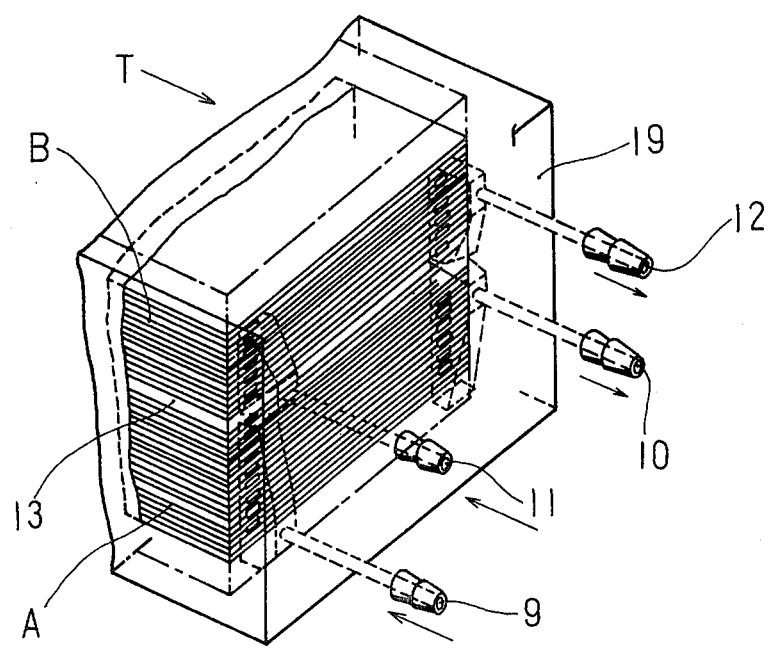
FIG. 10 is a perspective view of dialyzing liquid side of the dialyzing vessel.
Figure 11:
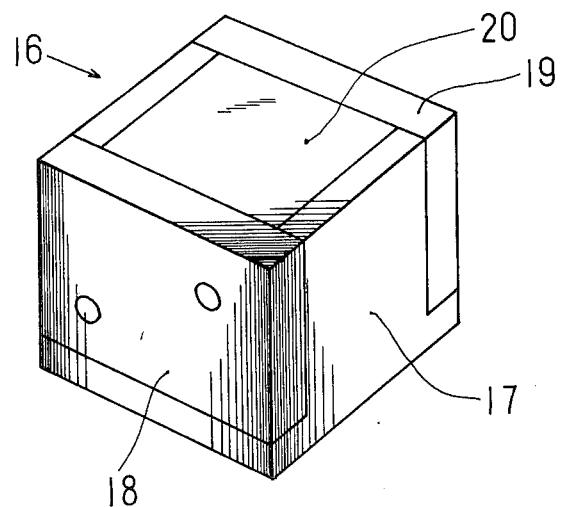
FIG. 11 is a perspective view of a case of the dialyzing vessel.

Referring to FIGS. 9 and 10, the dialyzing vessel T is divided into a negative pressure part A and a positive pressure part B. The upper surface of the lower holding plate 6 and the lower surface of the upper holding plate 5 together constitute a set of layer structure, and the dialyzing membrane 1 of semipermeable property is interposed between both surfaces so that the dialyzing element S is constituted. Several sets of the layer structure are laminated in the negative pressure part A and the positive pressure part B. Blood flows in an inlet 7 and out of an outlet 8. The dialyzing liquid 4 enters an inlet 9 in the negative pressure part A and flows out of an outlet 10 in the part A. The dialyzing liquid 4 enters an inlet 11 in the positive pressure part B and flows out of an outlet 12 in the part B. Numeral 13 designates a partition plate between the negative pressure part A and the positive pressure part B. Numeral 14 designates a bottom plate, and numeral 15 designates a top plate. The dialyzing vessel T is enclosed in a case 16 as illustrated in FIG. 11. The case 16 consists of a body 17, a side plate 18 for blood, another side plate 19 for dialyzing liquid, and a cover 20.

A method of removing toxins by means of said dialyzing vessel T will be explained. Referring to FIG. 12, FIG. 9 and FIG. 10, arterial blood from a human body enters the negative pressure part A of the dialyzing vessel T from the inlet 7. In the part A, waste products and harmful substances, such as toxins are removed during the passage through the dialyzing element S. Further the blood circulates in the positive pressure part B where filling-up substances from the dialyzing liquid 4 are added to the blood, thereby the qualified blood flows from the outlet 8 and circulates into the human body.

On the other hand, the dialyzing liquid 4 within a storage tank 21 flows through a pressure adjusting valve 22 and enters the positive pressure part B of the dialyzing vessel T from the inlet 11. The positive pressure part B which is adjusted in positive pressure supplies the above mentioned filling-up substances from the dialyzing liquid 4 to the blood by means of osmosis thereby the blood is qualified. Further the dialyzing liquid 4 flows from the outlet 12 into a pulse pressure adjusting valve 23.

The pressure adjusting valve 23 is periodically operated by means of a cam rotated by a motor M in a pulse generator 24, resulting in pulse variation of pressure in the dialyzing liquid 4. The pulse pressure is transmitted to the negative pressure part A in the dialyzing vessel T from the inlet 9, and acts on the dialyzing element. In addition, the pulse variation of pressure may be produced by operating the pulse pressure adjusting valve 23 using the action of the abdominal muscle caused by respiration of a human body in place of the pulse generator.

Referring to FIG. 13, there are innumerable discharge holes 25 scattered on the dialyzing membrane 1 of the capsule form. Each of the discharge holes 25 intermittently performs a rapid decrease or increase of the diameter corresponding to tension variation of the membrane surface. This expanding and contracting action is continuously repeated. Of course, harmful substances which are contained in blood and which are smaller than the diameter of the discharge hole 25 can be removed. Even in the case of larger substances than the discharge hole 25, an organic toxin particle M of higher or medium molecular weight, being a viscous and elastic body, can be removed due to the expanding and contracting action of the discharge hole 25, the toxin particles are pushed by pressure difference between blood and dialyzing liquid and by osmotic pressure, and then squeezed out of the discharge hole 25. This is because the decrease of the diameter produces strain within the toxin particle M, and in the accumulation state of the strain force the particles expand due to the expansion of the discharge hole 25 and are pushed in by means of the pressure difference and the osmotic pressure. Repetition of the action causes the toxin M to be squeezed and exhausted in the ambient dialyzing liquid. In this condition, useful substances such as amino acid, vitamins, and hormones are not exhausted from the discharge holes 25 during the expanding and contracting action, because these substances are as large as toxin particle M and flow in blood-plasma on account of their small viscosity.

The dialyzing liquid 4 which leaves the negative pressure part A passes through the outlet 10, a gas removing tank 26, a volume pump 27 and a filtering vessel 28, and is returned into a storage tank 21. Gases contained in the dialyzing liquid are exhausted outwards via an exhausting pump 29.

Figure 12A:
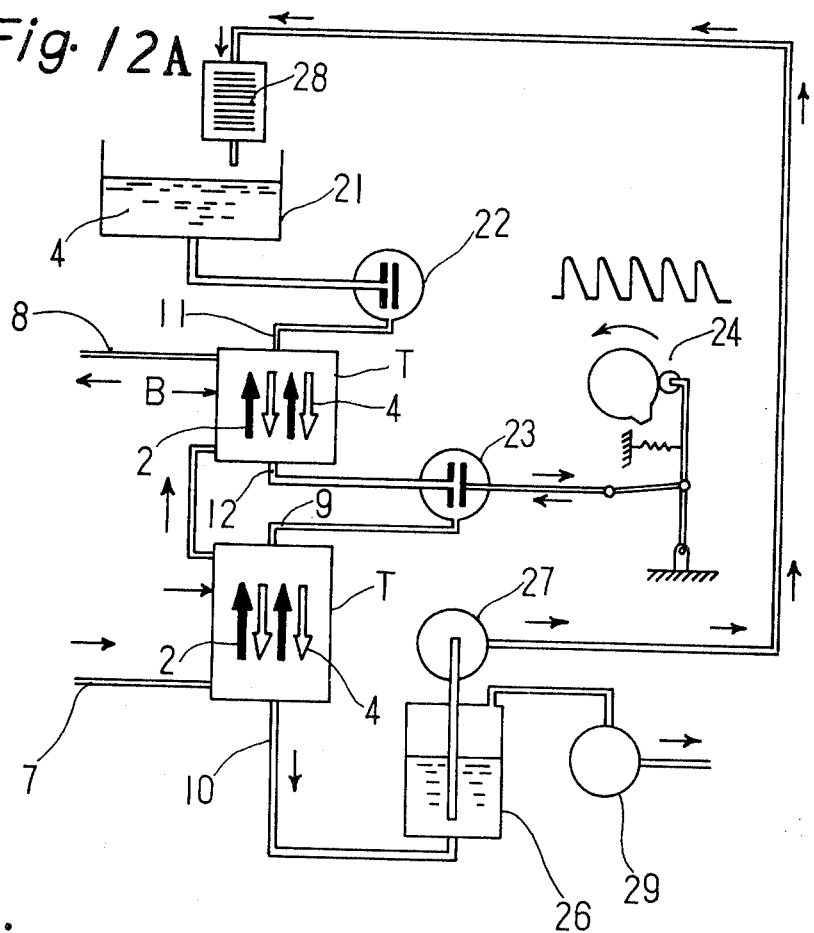
FIG. 12A is a flow sheet illustrating that pulse pressure is applied to the dialyzing liquid and harmful substances are removed in the negative pressure part of the dialyzing vessel, and filling-up substances are added to the blood from the dialyzing liquid in the positive pressure part.
Figure 12B:
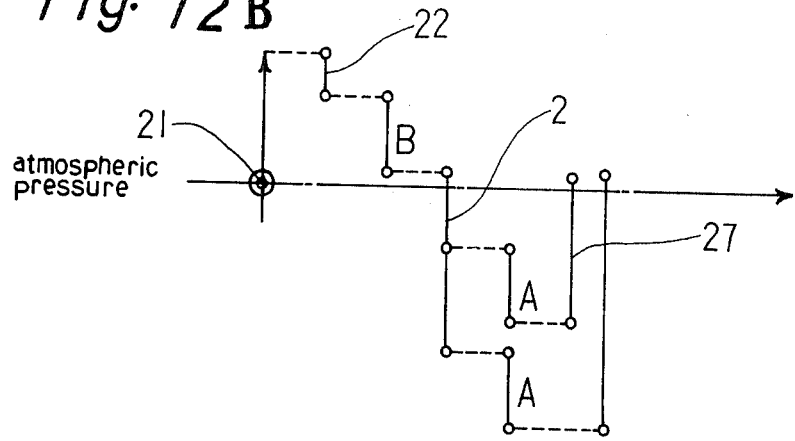
FIG. 12B is a graph illustrating the state of pressure in various parts of FIG. 12A.

FIG. 12B illustrates the relative pressure of the dialyzing liquid within the dialyzing vessel T and the pumps shown in FIG. 12A with respect to the atmospheric pressure, wherein the positive pressure part B is in positive pressure with respect to the atmospheric pressure, and the negative pressure part A in negative pressure.

Figure 14:
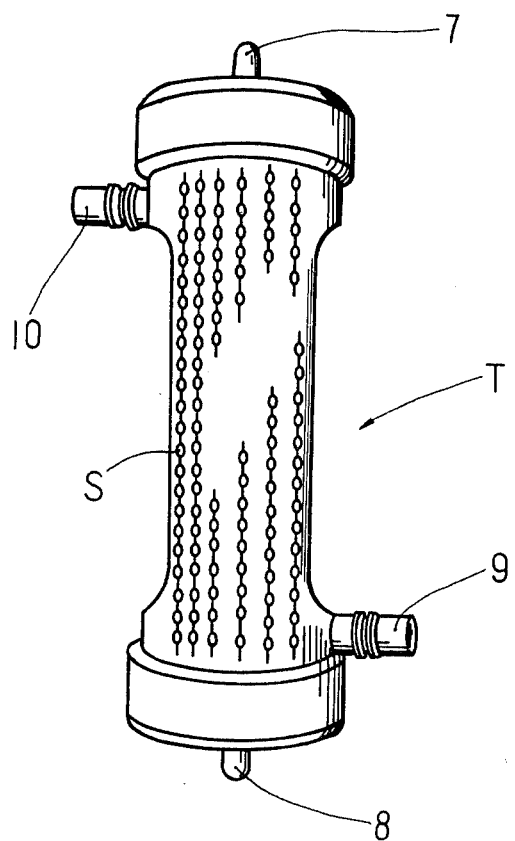
FIG. 14 is a perspective view of a dialyzing vessel of hollow pipe type provided with dialyzing elements.

The blood circulation path in said dialyzing element S may be utilized in a dialyzing vessel of hollow pipe type (called also hollow fiber type). This is show in FIG. 14.

Figure 15:
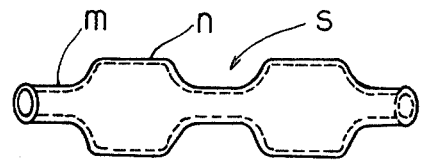
FIG. 15A is a schematic view of blood circulation path of hollow fiber type wherein small diameter portions are partly constituted.
FIG. 15B is a schematic view of blood circulation path of hollow fiber type wherein the pipe is partly depressed.
FIG. 15C and FIG. 15D are schematic views of FIG. 15B.
FIG. 15E and FIG. 15F are schematic sectional views of blood circulation path.
Figure 15:
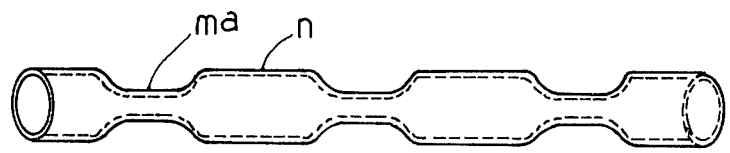
Figure 15:
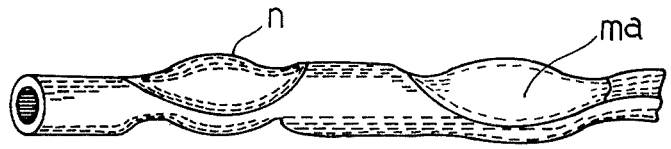
Figure 15:
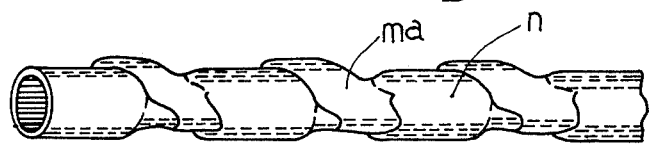
Figure 15:
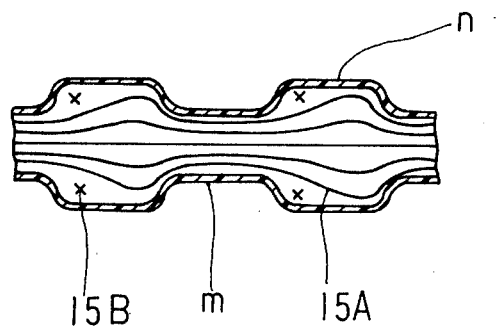
Figure 15:
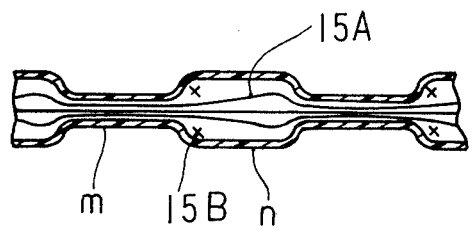

Referring to FIG. 15, there is shown an embodiment of a blood circulation path of so-called hollow fiber type wherein the blood circulation path in the dialyzing element S is constituted by hollow fiber. In general, the inner diameter of a pipe in use is about 0.4 mm~0.1 mm. The circulation path m of a small diameter is constituted as a small diameter pipe m shown in FIG. 15A or a depressed pipe ma shown in FIG. 15B (perspective view in FIG. 15C and FIG. 15D).

Referring to FIG. 15E and FIG. 15F, blood flows along a stream line 15A in the dialyzing element. In a position 15B designated as "X", blood-plasma comprises the isolated plasma layer. When a pressure variation is applied to the dialyzing liquid, the inner volume is suddenly decreased from the large diameter path n of the capsule form to the small diameter path m. Therefore, the influence of flow rate variation of blood caused by the pressure variation is small, and the effect of tension variation appears on the dialyzing membrane surface corresponding to the pressure variation.

Figure 3:
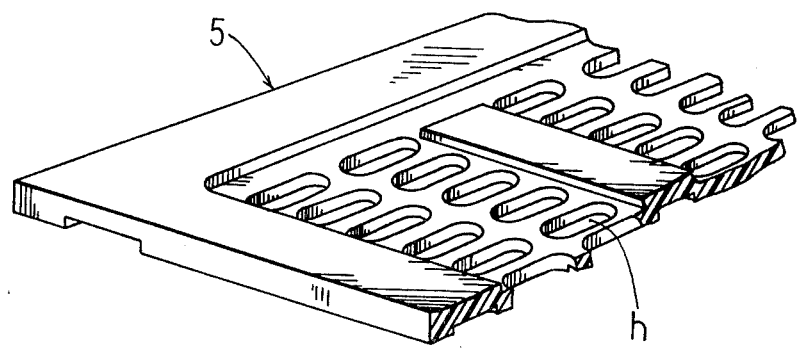
FIG. 3 is a perspective view of a part of an upper holding plate.
Figure 4:
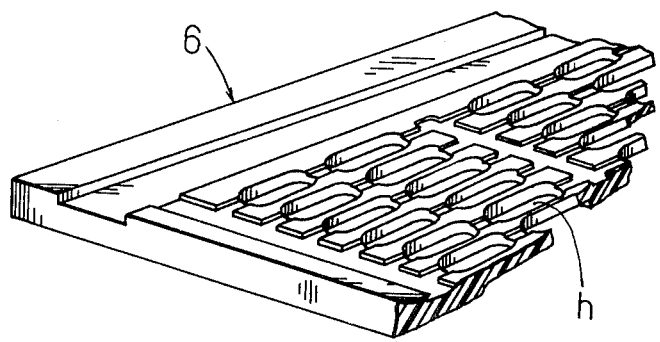
FIG. 4 is a perspective view of a part of a lower holding plate.

The dialyzing membrane 1 constituted in coil type by a flat membrane or laminated type is known. Embodiment in FIG. 3 and FIG. 4 illustrates many dialyzing elements S arranged in parallel. It can be seen that many dialyzing elements are closely arranged in parallel, and further that the marginal membranes between adjacent elements are removed so as to constitute a dialyzing element group. Above embodiment is shown in FIG. 16.

In FIG. 16A, dialyzing membrane 1 is arranged along a flat holding plate 16A, blood flow $\alpha$ passes through blood circulation path $\beta$, and a number of dialyzing elements 16B are arranged in parallel. In FIG. 16B, stream line 16C of blood and plasma layer 16D in the dialyzing elements are shown. FIG. 16C illustrates sectional side elevation of dialyzing elements 16B.

In the above embodiment, blood flows from four circulation paths $\beta 1$, $\beta 2$, $\beta 3$ and $\beta 4$ into one dialyzing element group 16B or in reverse direction.

The present invention provides a dialyzing method of blood by applying a tension variation to a dialyzing membrane surface and repeatedly expanding and contracting discharge holes, therefore toxins and other harmful substances can be selectively removed by utilizing their viscosity. Dialyzing efficiency is significantly improved in the constitution that the dialyzing vessel is made in dialyzing element structure and the blood circulation path of a capsule form is made of dialyzing membrane. As a result, the dialyzing vessel can be made in very small size. In calculation, it can be made to a dimension of 1/20 in relation to a conventional type. In addition, the pulse variation of pressure may be produced by operating the pulse pressure adjusting valve using the action of abdominal muscle caused by respiration of a human body in place of the pulse generator, therefore the apparatus can be easily made in a smaller size. So the apparatus can be attached to a human body, resulting in an excellent effect.

I claim:

1. A method of dialyzing blood in an artificial kidney comprising the steps of:
   (a) withdrawing blood from the circulatory system of a living being;
   (b) directing said blood to an inlet of an artificial kidney, wherein said blood is forced through a blood circulation path comprised of a dialyzing membrane, said membrane having walls in contact with a dialyzing vessel, said vessel having a negative pressure area and a positive pressure area, and a dialyzing liquid circulating through said areas in said vessel;
   (c) applying pulse pressure variations to said dialyzing liquid when said liquid is in said negative pressure area, thus including tension variations on a surface of said dialyzing membrane and isolating blood plasma from the blood onto a peripheral portion of said walls of said membrane, said membrane having a plurality of discharge holes which are repeatedly expanded and contracted in response to said pulse pressure variations to selectively force particles smaller than the diameter of said, holes and toxins contained in the blood through said holes; and
   (d) adding filling-up substances contained in said dialyzing liquid in said positive pressure area to the blood by means of osmotic pressure.

2. A method of dialyzing blood in an artificial kidney as in claim 1 wherein said blood circulation path is comprised of a plurality of dialyzing elements connected consecutively, said dialyzing membrane walls being expanded in capsule form, and wherein said isolated blood-plasma is positioned so that the depth of a plasma layer is greatest at both ends of said dialyzing elements, and said dialyzing liquid is brought into contact with an expanded surface of said capsule so that harmful substances within said blood are dialyzed.

3. A method of dialyzing blood as in any of claims 1 or 2 wherein said artificial kidney further includes a pulse-pressure adjusting valve, said valve being operated so as to apply said pulse pressure variations in a manner corresponding to the action of the abdominal muscle of the human body.

* * * * *